United States Patent [19]

Blankley

[11] Patent Number: 4,503,043
[45] Date of Patent: Mar. 5, 1985

[54] SUBSTITUTED ACYL DERIVATIVES OF OCTAHYDRO-1H-ISOINDOLE-1-CARBOXYLIC ACIDS

[75] Inventor: Clifton J. Blankley, Ann Arbor, Mich.

[73] Assignee: Warner-Lambert Company, Morris Plains, N.J.

[21] Appl. No.: 387,985

[22] Filed: Jun. 14, 1982

Related U.S. Application Data

[60] Division of Ser. No. 327,651, Dec. 7, 1981, , which is a continuation-in-part of Ser. No. 235,381, Feb. 17, 1981, abandoned.

[51] Int. Cl.$^3$ .................... A61K 37/00; C07C 103/52
[52] U.S. Cl. ................ 514/10; 260/112.5 R; 548/512; 548/515; 548/470; 548/472; 514/416
[58] Field of Search .............. 548/512, 515; 424/274, 424/177; 260/112.5 R

[56] References Cited

U.S. PATENT DOCUMENTS

| | | | |
|---|---|---|---|
| 3,929,830 | 12/1975 | Richter et al. | 260/326.1 |
| 4,048,321 | 9/1977 | Beregi et al. | 548/515 |
| 4,116,962 | 9/1978 | Ondetti et al. | 424/274 |
| 4,129,566 | 12/1978 | Ondetti et al. | 546/326 |
| 4,154,840 | 5/1979 | Ondetti et al. | 424/267 |
| 4,154,935 | 5/1979 | Ondetti et al. | 546/189 |
| 4,234,489 | 11/1980 | Ondetti et al. | 260/326.42 |
| 4,296,110 | 10/1981 | Johnson | 424/244 |
| 4,350,704 | 9/1982 | Hoefle et al. | 424/274 |
| 4,385,180 | 5/1983 | Kim et al. | 424/274 |
| 4,404,206 | 9/1983 | Vincent et al. | 424/258 |

FOREIGN PATENT DOCUMENTS

| | | |
|---|---|---|
| 0012401 | 6/1980 | European Pat. Off. . |
| 0050800 | 5/1982 | European Pat. Off. . |

OTHER PUBLICATIONS

Derwent Abstract of Belgium Patent 873,092, Published, Jun. 1979.
Derwent Abstract of Germany Patent 2,720,996, Published, Nov. 1977.
Derwent Abstract of Belgium Patent 871,574, Published, Apr. 1979.
European Patent Publication No. 50–800 filed Oct. 15, 1981, published May 5, 1982, (Claiming Priority from U.S. Ser. No. 199,886 and U.S. Ser. No. 258,484).

*Primary Examiner*—Delbert R. Phillips
*Attorney, Agent, or Firm*—Joan Thierstein

[57] ABSTRACT

Substituted acyl derivatives of octahydro-1H-isoindole-1-carboxylic acid compounds and the pharmaceutically acceptable salts thereof are produced by acylating a suitably substituted octahydro-1H-isoindole with a suitably activated substituted carboxylic acid and when desired hydrolyzing the resulting product. The compounds of the invention, their salts and pharmaceutical compositions thereof are useful as antihypertensive agents.

7 Claims, No Drawings

SUBSTITUTED ACYL DERIVATIVES OF OCTAHYDRO-1H-ISOINDOLE-1-CARBOXYLIC ACIDS

CROSS REFERENCE TO RELATED APPLICATION

This application is a division of copending application Ser. No. 327,651, filed Dec. 7, 1981 which is a continuation-in-part of copending application Ser. No. 235,381 filed Feb. 17, 1981 and now abandoned.

SUMMARY AND DETAILED DESCRIPTION

The invention relates to octahydro-2-(ω-mercaptoalkanoyl)-1H-isoindole-1-carboxylic acid compounds having the formula

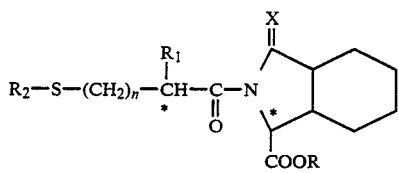

wherein R is hydrogen or lower alkyl; $R_1$ is hydrogen, lower alkyl, or benzyl; $R_2$ is hydrogen or

where $R_3$ is lower alkyl, heteroaryl containing 4 to 9 carbon atoms and one or two nitrogen, oxygen or sulfur atoms; phenyl having 1 or 2 substituents selected from the group consisting of fluorine, chlorine, bromine, lower alkyl, or lower alkoxy; n is 0 or 1, =X is

and pharmaceutically acceptable salts of the compounds when R is hydrogen and when $R_3$ is heteroaryl containing 1 or 2 nitrogen atoms. The terms lower alkyl and lower alkoxy include groups having straight or branched chains and containing 1 to 4 carbon atoms.

The invention further relates to substituted acyl derivatives of octahydro-1H-isoindole-1-carboxylic acid compounds having the formula

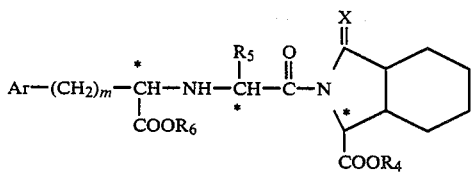

and pharmaceutically acceptable salts thereof wherein $R_4$ and $R_6$ are hydrogen or lower alkyl, $R_5$ is hydrogen, lower alkyl or benzyl; Ar is phenyl or phenyl substituted with 1 or 2 substituents selected from the group consisting of fluorine, chlorine, bromine, lower alkyl, lower alkoxy, hydroxy or amino; and m is 0 to 3, =X is

The terms lower alkyl and lower alkoxy include groups having straight or branched chains and containing 1 to 4 carbon atoms.

Preferred compounds of the invention are octahydro-2-(ω-mercaptoalkanoyl)-1H-isoindole-1-carboxylic acids having the formula

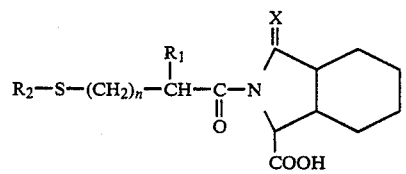

and pharmaceutically acceptable salts thereof; where $R_1$ is hydrogen or lower alkyl containing 1 to 3 carbon atoms; $R_2$ is hydrogen or

where $R_3$ is lower alkyl containing 1 to 3 carbon atoms, phenyl, furyl, benzo(b)furyl, thienyl, benzo(b)thienyl, pyridyl, quinolyl or isoquinolyl; and n is 0 or 1, =X is

Further preferred compounds of the invention are octahydro-2-(3-mercaptopropanoyl)-1H-isoindole-1-carboxylic acids having the formula

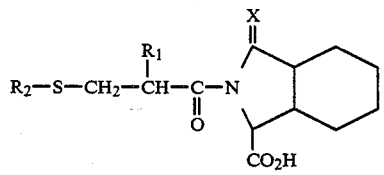

and pharmaceutically acceptable basic salts thereof; where $R_1$ is hydrogen or methyl; and $R_2$ is hydrogen or

where $R_3$ is methyl or phenyl, =X is

The preferred specific compounds of the invention are:
octahydro-2-(3-mercaptopropanoyl)-1H-isoindole-1-carboxylic acid;

octahydro-2-(3-mercapto-2-methylpropanoyl)-1H-isoindole-1-carboxylic acid;

octahydro-2-[3-(acetylthio)propanoyl]-1H-isoindole-1-carboxylic acid;

octahydro-2-[3-(acetylthio)-2-methylpropanoyl]-1H-isoindole-1-carboxylic acid;

octahydro-2-(3-mercaptopropanoyl)-3-oxo-1H-isoindole-1-carboxylic acid;

octahydro-2-(3-mercapto-2-methylpropanoyl)-3-oxo-1H-isoindole-1-carboxylic acid; and the pharmaceutically acceptable basic salts thereof.

Also preferred compounds of the invention are acylated octahydro-1H-isoindole-1-carboxylic acids having the formula

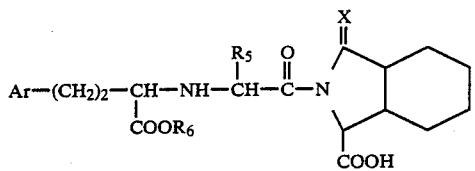

and the pharmaceutically acceptable salts thereof; where $R_5$ is hydrogen or lower alkyl containing 1 to 3 carbon atoms; $R_6$ is hydrogen or lower alkyl containing 1 to 3 carbon atoms; and Ar is phenyl, and phenyl substituted in the para position by fluorine, chlorine, bromine, methyl, hydroxy, methoxy or amino, and =X is

Further preferred compounds of the invention are acylated octahydro-1H-isoindole-1-carboxylic acids having the formula

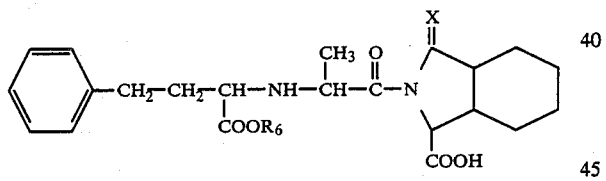

and the pharmaceutically acceptable salts thereof; where $R_6$ is hydrogen, lower alkyl of 1 to 3 carbon atoms, and =X is

and specifically the compounds designated 2-[2-[(1-carboxy-3-phenylpropyl)amino]-1-oxopropyl]octahydro-1H-isoindole-1-carboxylic acid; 2-[2-[(1-carbomethoxy-3-phenylpropyl)amino]-1-oxopropyl]octahydro-1H-isoindole-1-carboxylic acid; 2-[2-[(1-carbethoxy-3-phenylpropyl)amino]-1-oxopropyl]octahydro-1H-isoindole-1-carboxylic acid; 2-[2-[(1-carboxy-3-phenylpropyl)amino]-1-oxopropyl]octahydro-3-oxo-1H-isoindole-1-carboxylic acid; 2-[2-[(1-carbethoxy-3-phenylpropyl)amino]-1-oxopropyl]octahydro-3-oxo-1H-isoindole-1-carboxylic acid and the pharmaceutically acceptable salts thereof.

The compounds of the invention have asymmetric carbon atoms. These carbon atoms are indicated by an asterisk in formula I and II. Additional asymmetric carbon atoms may be present in the lower alkyl groups. The compounds accordingly exist as optical isomers and diastereomers or as racemates and mixtures thereof. All of these are within the scope of the invention. The S configuration at the centers marked with an asterisk in formulas I and II is preferred.

The octahydro-1H-isoindole-1-carboxylic acid and the octahydro-1H-isoindole-3-oxo-1-carboxylic acid used in this invention may potentially exist in several isomeric forms. The stereochemistry at the fused ring junction is believed to be cis. The carboxylic acid group may be either cis or trans to the fused cyclohexane ring.

The compounds of the invention may exist in anhydrous form as well as in solvated, including hydrated, forms. In general, the hydrated forms and the solvated forms with pharmaceutically acceptable solvents are equivalent to the anhydrous or unsolvated form for the purposes of the invention.

The compounds of the invention which have the formula

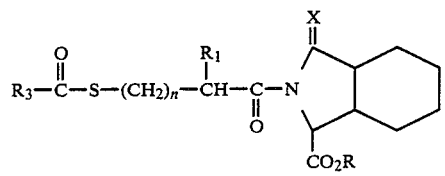

are produced by reacting octahydro-1H-isoindole-1-carboxylic acid compounds of formulas III and IV

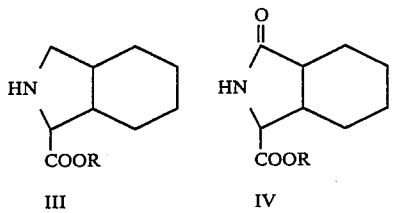

with an

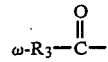

mercaptoalkanoic acid halide of formula V,

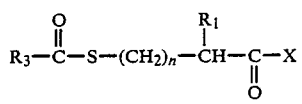

in a basic medium; where X is halogen, preferably chlorine or bromine; and R, $R_1$, $R_3$ and n have the significance specified above. The basic media can be provided preferably by the use of an excess of a tertiary organic amine such as pyridine or triethylamine, an alkali or alkaline earth metal hydroxide, an alkali metal bicarbonate, an alkali metal carbonate or other inorganic base capable of neutralizing the hydrogen halide formed during the reaction. The reaction is carried out at a temperature of about 0° C. to about 45° C. under anhydrous or aqueous conditions. Suitable organic solvents for the reaction include dichloromethane, tetrahydrofuran, dioxane, chloroform, pyridine and triethylamine. The reaction is quite rapid and is usually complete in about one-half to four hours.

The compounds of the invention wherein $R_2$ is an

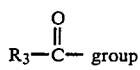 group and R is hydrogen can, in accordance with the invention, also be produced by reacting a trimethylsilyl ester of octahydro-1H-isoindole-1-carboxylic acid III and IV with an

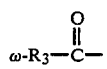

mercaptoalkanoic acid halide (V) followed by hydrolysis of the intermediate trimethylsilyl ester compound to the free acid by treatment with water. The first step of the process is carried out in a non-protic solvent such as methylene chloride, tetrahydrofuran, dioxane, chloroform or acetonitrile at an elevated temperature, usually about 60° C. to 100° C. After the reaction is complete, about one-half to one hour, the intermediate trimethylsilyl ester compound is treated with water at room temperature to produce the desired product.

The compounds of the invention wherein both R and $R_2$ are hydrogen which have the formula,

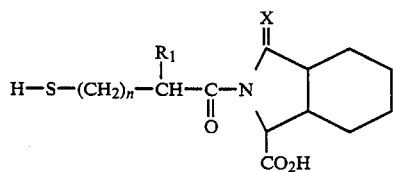

can, in accordance with the invention, be produced by hydrolyzing a compound of the invention which has the formula,

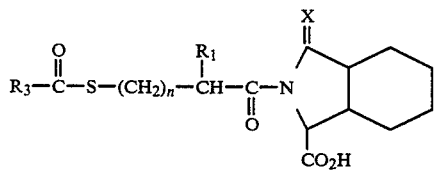

where R, $R_1$, $R_3$ and n have the same significance as given above. The hydrolysis is most conveniently carried out by reacting said compound with an excess of an alkali metal hydroxide in an aqueous alcoholic solution under an inert atmosphere for 5 minutes to 24 hours at a temperature of about 20° C. to about 80° C. The products wherein R and $R_2$ are both hydrogen can also be produced by ammonolysis of a compound of formula,

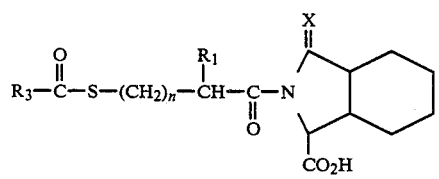

wherein $R_1$, $R_3$ and n have the same significance as given above. The ammonolysis is most conveniently carried out at room temperature in an alcohol which has been saturated with gaseous ammonia. The reaction usually requires 1 to 24 hours for completion.

The above described synthesis can utilize the racemate or one of the enantiomers as starting material. When the racemic starting material is used in the synthetic procedure, the diastereomers obtained in the product can be separated by conventional chromatographic or fractional crystallization methods.

Compounds of the invention of formula I where $R_2$ is

may alternately be prepared from compounds where $R_2$ is hydrogen by treatment of the latter with a suitable acylating agent,

where X is a leaving group; e.g., Cl, Br,

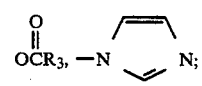

in the presence of a base, e.g., alkali carbonates or tertiary organic amines; in aprotic solvents, e.g., dimethylformamide, tetrahydrofuran or chlorinated hydrocarbons. These may be purified as the free acids or isolated as salts with hindered organic amines, e.g., dicyclohexylamine or t-butylamine.

The compounds of the invention of formula II may be prepared from octahydro-1H-isoindole-1-carboxylic acids III or IV by first protecting the carboxylic acid group, preferably as an ester, e.g., with a lower alkyl, benzyl or trimethylsilyl group. The protected carboxylic acid compound is coupled to an N-protected amino acid, e.g., glycine or L-alanine, protected on nitrogen with t-butyloxycarbonyl or benzyloxycarbonyl. The coupling is carried out by any of a variety of standard peptide coupling techniques as disclosed, for example, in "The Peptides. Analysis, Synthesis, Biology, Vol. 1, Major Methods of Peptide Bond Formation, Part A," ed. E. Gross, J. Meierhofer, Academic Press N.Y. (1979). An especially useful method involves the use of a dehydrating agent, such as dicyclohexylcarbodiimide alone or in the presence of reagents forming reactive esters, e.g., 1-hydroxybenztriazole, in suitable aprotic solvents such as dimethylformamide, acetonitrile, tetrahydrofuran or chlorinated hydrocarbons. This gives the intermediate N-protected-(2-aminoacyl)octahydro-1H-isoindole-1-carboxylic acid esters. These may then be either partially or totally deblocked depending on the protecting groups chosen, using anhydrous acids, e.g., hydrochloric acid in acetic acid or trifluoroacetic acid in dichloromethane or hydrogen gas and a catalyst to give the intermediate dipeptide either in free form or protected as an ester.

The compounds of the invention of formula II may then be prepared by reacting the intermediate dipeptide or its ester derivative with α-keto-4-substituted phenylbutyric acid or its lower alkyl ester derivatives under dehydrating and reducing conditions. Preferred dehydrating agents include molecular sieves in aprotic solvents and preferred reducing agents include sodium cyanoborohydride or hydrogen gas with a catalyst.

Alternatively, the dipeptide or its ester derivative may be reacted with an α-halo-4-substituted phenylbutyric acid or its ester in the presence of a suitable basic reagent, such as triethylamine or alkali carbonates or bicarbonates, in a solvent, to give the compounds of the invention of formula II. Ester protected products may be hydrolyzed under basic or acidic reaction conditions to free acid derivatives, or, in the case of benzyl esters, catalytic hydrogenolysis may be preferred.

Alternately, compounds of the invention of formula II may be prepared in a different manner. This consists of applying either of the two methods described above for the attachment of the 2-(4-phenylbuyric acid) moiety to the protected dipeptide, first to glycine or L-alanine, protected as an ester, to give N-[2-(4-phenylbutyric acid)]-substituted glycine or L-alanine derivative.

After selective deblocking of the acid moiety on the glycine or alanine portion of the product, the resulting monoacid may be coupled, either directly or subsequent to suitable blocking of the amino group, via standard peptide coupling procedures to the octahydro-1H-isoindole-1-carboxylic acids III or IV protected as an ester, i.e., $R_7$. Selective or complete removal of the ester groups and any amine protecting groups yield the compounds of formula II.

The products are obtained typically as a mixture of diastereomers which can be separated by standard methods of fractional crystallization or chromatography.

The compounds of this invention form basic salts with various inorganic and organic bases which are also within the scope of the invention. Such salts include ammonium salts, alkali metal salts like sodium and potassium salts, alkaline earth metal salts like the calcium and magnesium salts, salts with organic bases, e.g., dicyclohexylamine or benzathine, salts with basic amino acids like arginine, lysine and the like. The pharmaceutically acceptable salts are preferred, although other salts such as the dicyclohexylamine salt are also useful, e.g., in isolating, purifying or characterizing the product.

The salts are formed in conventional manner by reacting the free acid form of the product with one or more equivalents of the appropriate base providing the desired cation in a solvent or medium in which the salt is insoluble, or in water and removing the water by freeze drying.

In the compounds of formula I when $R_3$ is heteroaryl containing 1 or 2 nitrogen atoms and in the compounds of formula II the pharmaceutically acceptable acid addition salts may be prepared by conventional reactions with equivalent amounts of organic or inorganic acids. As exemplary, but not limiting, of pharmaceutically acceptable acid salts are the salts of hydrochloric, sulfuric, acetic, fumaric, malic, maleic and citric acids.

The action of the enzyme renin on angiotensinogen, a pseudoglobulin in blood plasma, produces the decapeptide angiotensin I. Angiotensin I is converted by angiotensin converting enzyme (ACE) to the octapeptide angiotensin II. The latter is an active pressor substance which has been implicated as the causative agent in various forms of hypertension in various mammalian species, e.g., rats and dogs. The compounds of this invention intervene in the renin->angiotensin I->angiotensin II sequence by inhibiting angiotensin I converting enzyme and reducing or eliminating the formation of the pressor substance angiotensin II, and therefore are useful in reducing or relieving hypertension. Thus by the administration of a composition containing one or a combination of compounds of formula I or a pharmaceutically acceptable salt thereof, hypertension in the species of mammal suffering therefrom is alleviated. A single dose, or preferably two to four divided daily doses, provided on a basis of about 0.1 to 100 mg per kilogram per day, preferably about 1 to 50 mg per kilogram per day is appropriate to reduce blood pressure. The substance is preferably administered orally, but parenteral routes such as subcutaneously, intramuscularly, intravenously or intraperitonealy can also be employed.

The following Table shows the in vitro activity of compounds of formula VI in an assay for angiotensin converting enzyme inhibitory activity which is a modification of a test reported by D. Cushman and H. Cheung, Biochemical Pharmacology, 20, 1637–1648 (1971).

In vitro ACE Assay: Angiotensin converting enzyme (ACE) inhibitory activity is determined by assaying guinea pig serum ACE in the presence and absence of the test compound. ACE from guinea pig serum and the test compounds are preincubated for 10 minutes before the addition of the labelled substrate $^3$H-hippurylglycylglycine. After a 60 minute incubation at 37° C. the reaction is stopped by the addition of 0.1N HCl. ACE cleaves the hippuryl-glycyl bond to form the dipeptide glycyl-glycine and $^3$H-hippuric acid. The $^3$H-hippuric acid is then extracted with ethyl acetate and the ACE inhibition of a given sample calculated on the basis of the $^3$H-hippuric acid generated.

TABLE

Activity of Compounds of Formula VI and VII

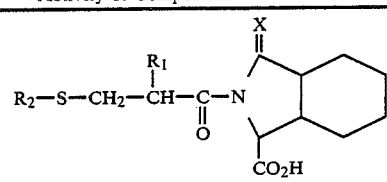

VI

| $R_1$ | $R_2$ | X | $IC_{50}$ (μM) |
|---|---|---|---|
| H | COCH$_3$ | H, H | 1.2 |
| H | H | H, H | 0.024 |
| CH$_3$ | COCH$_3$ | H, H | 0.42 |
| CH$_3$ | H | H, H | 0.028 |
| H | COCH$_3$ | O | 0.66 |
| H | H | O | 0.013 |
| CH$_3$ | COCH$_3$ | O | 0.28 |
| CH$_3$ | H | O | 0.014 |

TABLE-continued
Activity of Compounds of Formula VI and VII

VII

| R$_6$ | X | |
|---|---|---|
| CH$_2$CH$_3$ | H<br>⟨<br>H | 0.17 |
| H | H<br>⟨<br>H | 0.0026 |
| CH$_2$CH$_3$ | O | 0.34 |

The IC$_{50}$ is the molar concentration of compound which inhibits 50% of the conversion of angiotensin I to angiotension II.

The compounds of the invention can be utilized to reduce blood pressure in the form of tablets, capsules or elixirs for oral administration or in sterile solutions or suspensions for parenteral administration. About 10 to 500 mg. of a compound or mixture of compounds of formula I or a pharmaceutically acceptable salt is compounded with a pharmaceutically acceptable vehicle or carrier which may contain excipients, binders, preservatives, stabilizers, flavors, etc., in accord with accepted pharmaceutical practice. The amount of active substance in these compositions or preparations is such that a suitable dosage in the range indicated is obtained.

Illustrative of the inert ingredients which may be incorporated in tablets, capsules and the like are the following: A binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The invention is illustrated by the following examples.

EXAMPLE 1
2-[3-(Acetylthio)-1-oxopropyl]octahydro-1H-isoindole-1-carboxylic acid A mixture of 2.0 g of octahydro-1H-isoindole-1-carboxylic acid hydrochloride, 2.3 g of pyridine and 25 ml of tetrahydrofuran is cooled to 0° C. and treated dropwise with 3-(acetylthio)-propanoyl chloride. The mixture is stirred for 2 hours at 0° C. and allowed to warm to room temperature during another hour. The solvent is removed at reduced pressure. The residue is treated with water, acidified with 6N sulfuric acid and extracted with ethyl acetate. Drying, filtration, and concentration of the organic layer gives the crude product as an oil which solidifies. A pure sample is obtained after recrystallization from ethyl acetate and has mp 140°–145° C.

Octahydro-1H-isoindole-1-carboxylic acid hydrochloride used as an intermediate in this preparation is obtained by the following method. Following a procedure given in Gazz. Chim. Ital, 106, 65(1976), 2,3-dihydro-1H-isoindole-1-carboxylic acid, methyl ester, hydrochloride is prepared. This compound, 2.14 g, is dissolved in 100 ml of methanol and 5 ml of acetic acid and hydrogenated over 0.5 g of 10% rhodium/carbon catalyst. The catalyst is removed by filtration and the filtrate is concentrated to give a residue which solidifies on trituration with ether. Recrystallization from methanol-ether gives a pure sample of methyl octahydro-1H-isoindole-1-carboxylate hydrochloride, mp 181°–183° C.

This compound, 6.25 g, is combined with 17.5 ml of concentrated hydrochloric acid and 36 ml of water and heated at reflux for 4 hours. The solvent is removed at reduced pressure and the wet residue is recrystallized from water to give octahydro-1H-isoindole-1-carboxylic acid, hydrochloride, mp 257°–262° C. (dec).

EXAMPLE 2
2-(3-Mercaptopropanoyl)octahydro-1H-isoindole-1-carboxylic acid, dicyclohexylamine salt A solution of 1.2 g of 2-[3-(acetylthio)-1-oxopropyl]octahydro-1H-isoindole-1-carboxylic acid in 10 ml of 5N ammonia in methanol is prepared under nitrogen and allowed to stand for 2 hours. The solvent is removed at reduced pressure and the resulting residue is treated with 10% potassium bisulfate solution and extracted with ethyl acetate. The organic layer is dried and concentrated to give the crude product. This is purified as the dicyclohexylamine salt which is recrystallized from ethyl acetate, has mp 170°–175° C. (dec) and contains varying amounts of water of hydration.

SALTS

Sodium
Octahydro-2-(3-mercapto-2-methylpropanoyl)-1H-isoindole-1-carboxylic acid (5 mg) is dissolved in a solution of water (2.5 ml) and an equivalent amount of 1N sodium hydroxide. The solution is freeze dried to obtain the sodium salt.

Magnesium
Octahydro-2-(3-mercaptopropanoyl)-1H-isoindole-1-carboxylic acid (5 mg) magnesium oxide (49.5 mg) and water (10 ml) are stirred with slight heating until complete solution is obtained. Then the solvent is removed by freeze drying to obtain the magnesium salt.

Calcium

Octahydro-2-(3-mercaptopropanoyl)-1H-isoindole-1-carboxylic acid (5 mg) is dissolved in a mixture of calcium hydroxide (91 mg) and water (10 ml), and the solution is freeze dried to obtain the calcium salt.

Potassium

Octahydro-2-(3-mercaptopropanoyl)-1H-isoindole-1-carboxylic acid (5 mg) is dissolved in a mixture of an equivalent amount of potassium bicarbonate and water (10 ml) and freeze dried to obtain the potassium salt.

EXAMPLE 3

2-[3-(Acetylthio)-2-methyl-1-oxopropyl]octahydro-1H-isoindole-1-carboxylic acid

Following the procedure of Example 1 but using 3-(acetylthio)-2-methylpropanoyl chloride in place of 3-(acetylthio)propanoyl chloride, 2-[3-(acetylthio)-2-methyl-1-oxopropyl]octahydro-1H-isoindole-1-carboxylic acid is prepared. This oil has an $R_f$ of 0.54 (silica gel; 1:1 chloroform/methanol).

EXAMPLE 4

2-[3-Mercapto-2-methyl-1-oxopropyl]octahydro-1H-isoindole-1-carboxylic acid

Following the procedure of Example 2, 2-[3-(acetylthio)-2-methyl-1-oxopropyl]octahydro-1H-isoindole-1-carboxylic acid is converted to 2-[3-mercapto-2-methyl-1-oxopropyl]octahydro-1H-isoindole-1-carboxylic acid, mp 119°–129° C. as the free acid; $R_f$=0.50 (silica gel; 1:1 chloroform/methanol).

EXAMPLE 5

2-[3-Acetylthio-1-oxopropyl]octahydro-3-oxo-1H-isoindole-1-carboxylic acid, dicyclohexylamine salt Octahydro-2-oxo-1H-isoindole-1-carboxylic acid, 1.5 g, in 20 ml of acetonitrile is stirred while 1.4 g of hexamethyldisilazane is added. A few drops of chlorotrimethylsilane is added as catalyst and the mixture is heated at reflux with protection from moisture for 5 hours. After removal of the solvent, the residue is dissolved in 20 ml of toluene and treated dropwise with 3-(acetylthio)propanoyl chloride. The solution is distilled slowly under partial reflux until the head temperature reaches 85° C. The remaining solvent is then removed under reduced pressure and the residual oil is partitioned between ethyl acetate and water. The organic layer is dried and concentrated at reduced pressure to give crude product. This may be purified by chromatography over silica gel, eluting with a 95:5:1 mixture of chloroform/methanol/acetic acid. The product is further purified as its dicyclohexylamine salt, which has mp 198°–203° C. after recrystallization from acetonitrile. The product may contain varying amounts of water of hydration.

The intermediate octahydro-3-oxo-1H-isoindole-1-carboxylic acid is prepared as follows. 2,3-Dihydro-3-oxo-1H-isoindole-1-carboxylic acid (J. Prakt. Chem., 146, 307(1936)), 20 g is heated at reflux for 2 hours with 250 ml of absolute ethanol and 5.6 g of concentrated sulfuric acid. On cooling, the solution deposits crystalline ethyl 2,3-dihydro-3-oxo-1H-isoindole-3-carboxylate. Recrystallization of this from ethanol gives pure material, mp 178°–183° C.

This ester, 15 g, is dissolved in 110 ml of tetrahydrofuran and 110 ml of absolute ethanol, treated with 1.0 g of 10% Rh/C catalyst and hydrogenated at an initial pressure of 50 psi and 36° C. After the required amount of hydrogen has been absorbed, the mixture is filtered and the filtrate is concentrated to give the crude product. Pure ethyl octahydro-3-oxo-1H-isoindole-1-carboxylate has mp 149°–157° C. after recrystallization from ethanol.

This ester, 5 g, is hydrolyzed by treating it with a mixture of 48 ml 1N sodium hydroxide and 10 ml of ethanol overnight at room temperature. Partial concentration to remove ethanol and acidification precipitates the crude acid. Octahydro-3-oxo-1H-isoindole-1-carboxylic acid has mp 205°–213° C. (decomposition) after recrystallization from water.

EXAMPLE 6

2-[3-Mercapto-1-oxopropyl]octahydro-3-oxo-1H-isoindole-1-carboxylic acid, dicyclohexylamine salt A mixture of 1.6 g of 2-[3-(acetylthio)-1-oxopropyl]octahydro-3-oxo-1H-isoindole-1-carboxylic acid, dicyclohexylamine salt and a solution of 1.8 g of potassium bisulfate in 80 ml of water is stirred for 10 minutes. The free carboxylic acid is extracted into ethyl acetate and the organic layer is dried and concentrated under reduced pressure. The residue is then hydrolyzed following the procedure of Example 2. The product is isolated as a dicyclohexylamine salt, mp 188°–208° C. after recrystallization from acetonitrile.

EXAMPLE 7

2-[3-(Acetylthio)-2-methyl-1-oxopropyl]octahydro-3-oxo-1H-isoindole-1-carboxylic acid, dicyclohexylamine salt.

This compound is prepared following the procedure of Example 5 using 3-acetylthio-2-methylpropanoyl chloride as intermediate. The product is purified by recrystallization from ethyl acetate and has mp 185°–188° C.

EXAMPLE 8

2-[3-(Mercapto-2-methyl-1-oxopropyl]octahydro-3-oxo-1H-isoindole-1-carboxylic acid, dicyclohexylamine salt This compound is prepared from 2-[3-(acetylthio)-2-methyl-1-oxopropyl]octahydro-3-oxo-1H-isoindole-1-carboxylic acid following the procedure of Example 2. The dicyclohexylamine salt is prepared and has mp 191°–200° C. after recrystallization from acetonitrile.

EXAMPLE 9

1000 tablets each containing 100 mg of octahydro-2-(3-mercaptopropanoyl)-1H-isoindole-1-carboxylic acid are produced from the following ingredients.

| | |
|---|---|
| Octahydro-2-(3-mercaptopropanoyl)-1H—isoindole-1-carboxylic acid | 100 g |
| Corn Starch | 50 g |
| Gelatin | 7.5 g |
| Avicel (microcrystalline cellulose) | 25 g |
| Magnesium Stearate | 2.5 g |

The octahydro-2-(3-mercaptopropanoyl)-1H-isoindole-1-carboxylic acid and corn starch are admixed with an aqueous solution of the gelatin. The mixture is dried and ground to fine powder. The Avicel and then the magnesium stearate are admixed with the granulation. This is then compressed in a tablet press to form 1000 tablets each containing 100 mg of active ingredients.

EXAMPLE 10

Two piece No. 1 gelatin capsules each containing 250 mg of octahydro-2-(3-mercaptopropanoyl)-1H-isoindole-1-carboxylic acid are filled with a mixture of the following ingredients.

| | |
|---|---|
| Octahydro-2-(3-mercaptopropanoyl)-1H—isoindole-1-carboxylic acid | 250 mg |
| Magnesium Stearate | 7 mg |
| USP Lactose | 193 mg |

EXAMPLE 11

An injectable solution is produced as follows:

| | |
|---|---|
| Octahydro-2-(3-mercaptopropanoyl)-1H—isoindole-1-carboxylic acid, sodium salt | 500 g |
| Methyl Paraben | 5 g |
| Propyl Paraben | 1 g |
| Sodium Chloride | 25 g |
| Water for Injection q.s. | 5 g |

The active substance, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

EXAMPLE 12

2-[2-[(1-Carbethoxy-3-phenylpropyl)amino]-1-oxopropyl]-octahydro-1H-isoindole-1-carboxylic acid, hydrochloride A mixture of 6.5 g of t-butyl octahydro-1H-isoindole-1-carboxylate hydrochloride, 7.0 g of (S,S)ethyl α-[(1-carboxyethyl)amino]benzenebutanoate (prepared by neutralization of the hydrochloride salt), 3.4 g of hydroxybenztriazole and 2.5 g of triethylamine in 125 ml of tetrahydrofuran is stirred and cooled to 0° C. while a solution of 5.2 g of dicyclohexylcarbodiimide in 15 ml of tetrahydrofuran is added dropwise. The mixture is stirred at 0° C. for one hour, and then allowed to warm to room temperature overnight. The mixture is filtered and the filtrate is concentrated at reduced pressure. The residue is taken up in ethyl acetate and the mixture is filtered again, washed successively with saturated sodium bicarbonate solution and saturated sodium chloride solution, dried and concentrated at reduced pressure to give product as an oily mixture of two isomers. The desired, more active isomer (presumed to have the S configuration at centers designated with an asterisk in formula II) is separated after chromatography over silica gel, eluting with a 99:1 chloroform/methanol mixture and collecting the product isomer first eluted. This is an oil with $[\alpha]_D^{23} = -45.0°$ (c=1.08, ethanol).

This preferred diester is converted to the corresponding monoethyl ester by dissolving it in methylene chloride, filtering to clarify the solution, cooling to 0° C. and bubbling hydrochloric acid gas through the solution for 15 minutes. After standing overnight at 0° C., the solution is concentrated to remove solvent. The residue is crystallized by treating an ethanol solution of it with ether. The desired product, (S,S,S)-2-[2-[(1-carbethoxy-3-phenylpropyl)amino]-1-oxopropyl]octahydro-1Hisoindole-1-carboxylic acid, hydrochloride has mp 198°–216° (dec.); $[\alpha]_D^{23} = -33.6°$ (c=1.07, ethanol), and $R_f = 0.09$ (silica gel; 95:1 chloroform/methanol, developed twice).

The intermediate (S,S)ethyl α-[(1-carboxyethyl)amino]benzenebutanoate hydrochloride used in this preparation may be prepared in the following manner. A solution of 2.0 g of t-butyl L-alanine and 3.78 g of ethyl 2-bromo-4-phenylbutanoate in 25 ml of dimethylformamide is treated with 1.8 ml of triethylamine and the solution is heated at 70° C. for 18 hours. The solvent is removed at reduced pressure and the residue is mixed with water and extracted with ethyl ether. The organic layer is washed with water and dried over magnesium sulfate. Concentration of the solvent at reduced pressure gives the oily t-butyl ester of the intermediate which is found to be sufficiently pure by gas liquid chromatography for further use.

A solution of 143.7 g of this t-butyl ester in 630 ml of trifluoroacetic acid is stirred at room temperature for one hour. The solvent is removed at reduced pressure and the residue is dissolved in ethyl ether and again evaporated. This operation is repeated. Then the ether solution is treated dropwise with a solution of hydrogen chloride gas is ethyl ether until precipitation ceases. The solid is collected by filtration and is a mixture of diastereoisomers, mp 153°–165° C., $[\alpha]_D^{23} = +3.6°$ (c=1, methanol).

In order to separate the preferred S,S isomer, a suspension of 10.0 g of the mixture in 200 ml of methylene chloride is stirred at room temperature for five minutes and filtered; the solid is washed with additional methylene chloride and finally ether. The solid material, mp 202°–208° C. (dec.), $[\alpha]_D^{23} = -29.3°$ (c=1, methanol) is the less preferred diastereoisomer having the R,S configuration (S referring to the portion derived from L-alanine). The preferred S,S diastereoisomer can be recovered from the filtrate after concentration and trituration of the residue with ether. It has mp 137°–139° C., $[\alpha]_D^{23} = +31.3°$ (c=1, methanol).

The t-butyl octahydro-1H-isoindole-1-carboxylate hydrochloride is prepared as follows. Following a procedure given in Gazz. Chim. Ital, 106, 65(1976), 56 g of (2-methylphenyl)acetyl chloride is converted to 2-bromo-(2-bromomethylphenyl)acetyl chloride. This is added dropwise to a solution of 78.6 g of t-butyl alcohol in 120 ml of ether and cooled at 0° C. Finally 26.4 g of pyridine is added. After a few minutes, the precipitated solids are filtered and washed with ether. The filtrate is washed successively with water and dilute sodium bicarbonate solution dried and concentrated at reduced pressure. t-Butyl 2-bromo-(2-bromomethylphenyl)acetate is obtained as an oil of sufficient purity for further use by chromatography over silica gel, eluting with a 4:1 hexane/ethyl acetate mixture.

A mixture of 11.5 g of this ester and 15 g of powdered anhydrous sodium bicarbonate in 100 ml of acetonitrile is cooled to 0° C. under nitrogen and treated dropwise with 3.7 g of benzylamine. The mixture is allowed to stand at room temperature for 64 hours, then filtered.

Concentration gives crude t-butyl 2,3-dihydro-2-(phenylmethyl)-1H-isoindole-1-carboxylate which is purified by conversion to the hydrochloride salt with hydrogen chloride gas in ether. The salt has mp 154°–157° C. after recrystallization from ethyl acetate.

The N-benzyl group is removed from this salt by hydrogenolysis is methanol solution over 20% Pd/C catalyst. The product, t-butyl 2,3-dihydro-1H-isoindole-1-carboxylate hydrochloride, is recrystallized from ethanol/ether and has mp 148°–156° C. (decomposition).

A solution of 13.8 g of this salt in 300 ml of a 7:1 t-butyl alcohol/tetrahydrofuran mixture is treated with 2 g of a 10% Rh/C catalyst and hydrogenated at 40° C. and 50 psi initial pressure. Additional time and catalyst may be required if hydrogen uptake is not complete. The desired t-butyl octahydro-1H-isoindole-1-carboxylate hydrochloride is obtained after filtration of the catalyst and concentration of the filtrate. It may be purified by recrystallization from ethanol/ether to give material with mp 173°–176° C.

EXAMPLE 13

2-[2-[(1-Carboxy-3-phenylpropyl)amino]-1-oxopropyl]-octahydro-1H-isoindole-1-carboxylic acid A solution of 0.7 g of 2-[2-([1-carbethoxy-3-phenylpropyl]amino]-1-oxopropyl]octahydro-1H-isoindole-1-carboxylic acid hydrochloride in 15 ml of absolute ethanol is treated with 0.5 g of potassium hydroxide pellets. The mixture is stirred at room temperature overnight, then filtered and the solvent is evaporated at reduced pressure. The residue is taken up in 50 ml of water and acidified to pH 3 with 4N hydrochloric acid. The product precipitates out and is recrystallized from absolute ethanol; mp 193°–197° C. $[\alpha]_D^{23} = -39.9°$.

EXAMPLE 14

2-[2-[(1-carbethoxy-3-phenylpropyl)amino]-1-oxopropyl]-octahydro-3-oxo-1H-isoindole-1-carboxylic acid, hydrochloride Following the procedure of Example 12, but substituting t-butyl octahydro-3-oxo-1H-isoindole-1-carboxylate for t-butyl octahydro-1H-isoindole-1-carboxylate gives the desired product as a mixture of isomers. This is further purified by dissolving it in water, filtering insolubles, and freeze-drying the filtrate. This gives an amorphous solid, mp 50°–70° (shrinks), 160° (decompose) with $[\alpha]_D^{23} = +9.5°$ (C=1.01, ethanol), $R_f$=0.05, 0.1 (silica gel; 95:1 chloroform/methanol, developed twice).

The intermediate t-butyl octahydro-3-oxo-1H-isoindole-1-carboxylate is prepared from octahydro-3-oxo-1H-isoindole-carboxylic acid (Example 5) as follows. A mixture of 10 g of this acid and 0.4 ml of 70% perchloric acid in 150 ml of t-butyl acetate is allowed to stand for 2.5 days. An additional 50 ml of t-butyl acetate is added and the reaction is allowed to continue for 15 days. The solution is filtered and poured onto 14 g of 50% sodium hydroxide solution and ice. The product is extracted into ether. Drying and concentration gives a residue which when triturated with hexane gives material, mp 143°–149° C., suitable for further use.

We claim:

1. A substituted acyl derivative of an octahydro-1H-isoindole-1-carboxylic acid having the formula

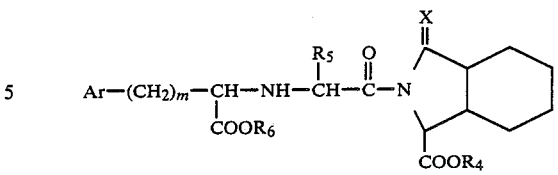

wherein $R_4$ is hydrogen or lower alkyl; $R_5$ is hydrogen, lower alkyl or benzyl; $R_6$ is hydrogen or lower alkyl; Ar is phenyl or phenyl substituted with 1 or 2 substituents selected from the group consisting of fluorine, chlorine, bromine, lower alkyl, lower alkoxy, hydroxy or amino; and m is 0 to 3, =X is O; wherein lower alkyl and lower alkoxy contain 1 to 4 straight or branched carbon atoms and the pharmaceutically acceptable basic salts thereof.

2. A substituted acyl derivative of an octahydro-1H-isoindole-1-carboxylic acid according to claim 1 having the formula

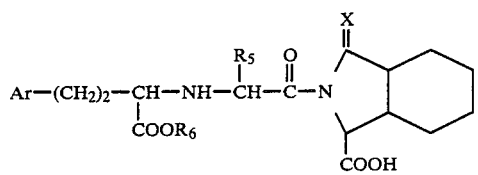

and the pharmaceutically acceptable salts thereof; where $R_5$ is hydrogen or lower alkyl containing 1 to 3 carbon atoms; $R_6$ is hydrogen or lower alkyl containing 1 to 3 carbon atoms; and Ar is phenyl, and phenyl substituted in the para position by fluorine, chlorine, bromine, methyl, hydroxy, methoxy or amino, =X is 0.

3. A substituted acyl derivative of an octahydro-1H-isoindole-1-carboxylic acid according to claim 2 having the formula

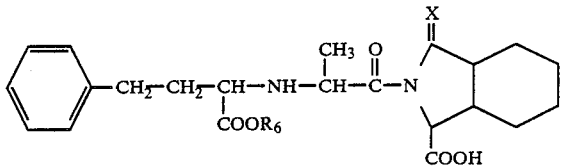

and the pharmaceutically acceptable salts thereof; where $R_6$ is hydrogen or lower alkyl containing 1 to 3 carbon atoms, =X is 0.

4. The compound according to claim 3 which is 2-[2-[(1-carboxy-3-phenylpropyl)amino]-1-oxopropyl]-octahydro-3-oxo-1H-isoindole-1-carboxylic acid and pharmaceutically acceptable salts thereof.

5. The compound according to claim 3 which is 2-[2-[(1-carbethoxy-3-phenylpropyl)amino]-1-oxopropyl]-octahydro-3-oxo-1H-isoindole-1-carboxylic acid and pharmaceutically acceptable salts thereof.

6. A pharmaceutical composition comprising an antihypertensive effective amount of a substituted acyl derivative of octahydro-1H-isoindole-1-carboxylic acid according to claim 1 or a pharmaceutically acceptable salt thereof and a pharmaceutically acceptable carrier.

7. A method of treating hypertension by administering an effective amount of a substituted acyl derivative of an octahydro-1H-isoindole-1-carboxylic acid according to claim 1 or a pharmaceutically acceptable salt thereof.

* * * * *